US011111205B2

(12) United States Patent
Preising et al.

(10) Patent No.: US 11,111,205 B2
(45) Date of Patent: Sep. 7, 2021

(54) PROCESS FOR PREPARING ALKANEDIOL AND DIALKYL CARBONATE

(71) Applicant: SHELL OIL COMPANY, Houston, TX (US)

(72) Inventors: Henri Preising, Sachsen-Anhalt (DE); Frederik Hendrik Van Der Steen, Amsterdam (NL); Garo Garbis Vaporciyan, Amsterdam (NL); Wolfgang Dirk Lose, Sachsen-Anhalt (DE); Silke Eva Sabine Leonhardt, Sachsen-Anhalt (DE)

(73) Assignee: SHELL OIL COMPANY, Houston, TX (US)

( * ) Notice: Subject to any disclaimer, the term of this patent is extended or adjusted under 35 U.S.C. 154(b) by 68 days.

(21) Appl. No.: 16/631,945

(22) PCT Filed: Jul. 16, 2018

(86) PCT No.: PCT/EP2018/069238
§ 371 (c)(1),
(2) Date: Jan. 17, 2020

(87) PCT Pub. No.: WO2019/016126
PCT Pub. Date: Jan. 24, 2019

(65) Prior Publication Data
US 2020/0172466 A1 Jun. 4, 2020

(30) Foreign Application Priority Data
Jul. 18, 2017 (EP) ..................... 17181886

(51) Int. Cl.
| | | |
|---|---|---|
| *C07C 68/065* | (2020.01) |
| *B01J 27/18* | (2006.01) |
| *B01J 37/03* | (2006.01) |
| *B01J 37/04* | (2006.01) |
| *B01J 37/08* | (2006.01) |
| *C01B 25/36* | (2006.01) |
| *C07C 29/48* | (2006.01) |

(52) U.S. Cl.
CPC ......... *C07C 68/065* (2013.01); *B01J 27/1802* (2013.01); *B01J 37/031* (2013.01); *B01J 37/04* (2013.01); *B01J 37/08* (2013.01); *C01B 25/36* (2013.01); *C07C 29/48* (2013.01)

(58) Field of Classification Search
None
See application file for complete search history.

(56) References Cited

U.S. PATENT DOCUMENTS

| | | |
|---|---|---|
| 3,803,201 A | 4/1974 | Gilpin et al. |
| 4,062,884 A | 12/1977 | Romano et al. |
| 4,181,676 A | 1/1980 | Buysch et al. |
| 4,691,041 A | 9/1987 | Duranleau et al. |
| 5,218,135 A | 6/1993 | Buysch et al. |
| 5,292,701 A | 3/1994 | Glemza et al. |
| 5,359,118 A | 10/1994 | Wagner et al. |
| 5,455,368 A | 10/1995 | Janisch et al. |
| 5,489,702 A | 2/1996 | Doya et al. |
| 6,262,210 B1 | 7/2001 | Tojo et al. |
| 7,453,007 B2 | 11/2008 | Buchanan et al. |
| 7,732,630 B2 | 6/2010 | Nisbet et al. |
| 8,148,566 B2 | 4/2012 | Tojo et al. |
| 2003/0078448 A1 | 4/2003 | Buchanan et al. |
| 2009/0270656 A1 | 10/2009 | Fukuoka et al. |

FOREIGN PATENT DOCUMENTS

| | | |
|---|---|---|
| AU | 2008201826 A1 | 5/2008 |
| CN | 103787296 A | 5/2014 |
| EA | 010304 B1 | 8/2008 |
| EP | 0180387 A2 | 5/1986 |
| EP | 0274953 A1 | 7/1988 |
| EP | 0598464 A1 | 5/1994 |
| EP | 1016648 A1 | 7/2000 |
| ES | 2355782 A1 | 3/2011 |
| JP | S5569525 A | 5/1980 |
| JP | S58150435 A | 9/1983 |
| JP | 2188541 A | 7/1990 |
| JP | H06239806 A | 8/1994 |
| JP | H08198817 A | 8/1996 |
| JP | H09278689 A | 10/1997 |
| WO | 9818720 A1 | 5/1998 |
| WO | 0174485 A1 | 10/2001 |
| WO | 03089400 A1 | 10/2003 |
| WO | 2004024658 A1 | 3/2004 |
| WO | 2007002744 A2 | 1/2007 |
| WO | 2009136233 A1 | 11/2009 |
| WO | 2011039113 A1 | 4/2011 |

OTHER PUBLICATIONS

Shi et al., "Amorphous Mesoporous Aluminophosphate as Highly Efficient Heterogeneous Catalysts for Transesterification of Diethyl Carbonate With Dimethyl Carbonate", Catalysis Communications, vol. 12, 2011, pp. 721-725.
Zhang et al., "Synthesis and Pore Formation Study of Amorphous Mesoporous Aluminophosphates in the Presence of Citric Acid", Journal of Colloid and Interface Science, 302, 2006, pp. 278-286.
Kanat, "Surface Properties and Catalytic Activity of Manganese Ferrospinels", Thesis, Apr., 2002, 2 pages.
Epling et al., "Reaction and Surface Characterization Study of Higher AlcoholSynthesis Catalysts", Journal of Catalysis, vol. 169, Issue No. Jul. 15, 1997, pp. 438-446.

(Continued)

*Primary Examiner* — Joseph R Kosack
(74) *Attorney, Agent, or Firm* — Shell Oil Company

(57) ABSTRACT

The invention relates to a process for the preparation of an alkanediol and a dialkyl carbonate comprising reacting an alkylene carbonate and an alkanol in the presence of a catalyst, wherein the catalyst is aluminum phosphate.

10 Claims, No Drawings

(56) References Cited

OTHER PUBLICATIONS

Epling et al., "Reaction and Surface Characterization Study of Higher Alcohol Synthesis Catalysts", Journal of catalysis, vol. 172, Issue no. 1, Nov. 1997, pp. 13-23.
Epling et al., "Reaction and Surface Characterization Study of Higher Alcohol Synthesis Catalysts: VII. Cs- and Pd-Promoted 1:1 Zn/Cr Spinel", Journal of Catalysis, vol. 175, Issue No. 2, Apr. 1998, pp. 175-184.
Minahan et al., "Reaction and Surface Characterization Study of Higher Alcohol Synthesis Catalysts: IX. Pd- and Alkali-Promoted Zn/Cr-Based Spinels Containing Excess ZnO", Journal of Catalysis, vol. 179, Issue No. 1, Oct. 1998, pp. 241-257.
International Search Report and Written Opinion received for PCT Patent Application No. PCT/EP2010/064153, dated Nov. 8, 2010, 08 pages.
Knifton et al., "Ethylene Glycol-dimethyl Carbonate Cogeneration", Journal of Molecular Catalysis, vol. 67, 1991, pp. 389-399.
International Search Report and Written Opinion received for PCT Patent Application No. PCT/EP2018/069238, dated Aug. 22, 2018, 9 pages.
Ullmann's Encyclopedia of Industrial Chemistry, 5th edition. vol. B4, 1992, pp. 321-328 ff.

PROCESS FOR PREPARING ALKANEDIOL AND DIALKYL CARBONATE

CROSS REFERENCE TO RELATED APPLICATIONS

This is a national stage application of International Application No. PCT/EP2018/069238, filed 16 Jul. 2018, which claims benefit of priority to European Patent Application No. 17181886.7, filed 18 Jul. 2017.

FIELD OF THE INVENTION

The present invention relates to a process for the preparation of an alkanediol and a dialkyl carbonate from an alkylene carbonate and an alkanol.

BACKGROUND OF THE INVENTION

Such process is for example disclosed in WO2004024658, which discloses the use of a zinc supported catalyst for the alcoholysis of alkylene carbonates. For example, WO2004024658 discloses the use of various zinc supported catalysts in the reaction of propylene carbonate with methanol (methanolysis of propylene carbonate) thereby producing monopropylene glycol (1,2-propanediol) and dimethyl carbonate. One of the used catalysts is a $Zn.Cr_2O_3$ catalyst.

A potential problem associated with such zinc supported catalysts is leaching of metals from the catalyst resulting in decreased catalyst activity over time. In addition, the metal chromium may not be a desired metal from an environmental perspective. Still further, generally, it is desired to provide a process for the preparation of an alkanediol and a dialkyl carbonate from an alkylene carbonate and an alkanol, wherein an alternative catalyst having an improved activity and/or selectivity is used. It is an object of the present invention to provide such process.

SUMMARY OF THE INVENTION

Surprisingly it was found that the above object may be achieved by use of aluminum phosphate as a catalyst.

Accordingly, the present invention relates to a process for the preparation of an alkanediol and a dialkyl carbonate comprising reacting an alkylene carbonate and an alkanol in the presence of a catalyst, wherein the catalyst is aluminum phosphate.

DETAILED DESCRIPTION OF THE INVENTION

In the context of the present invention, in a case where a catalyst or composition comprises two or more components, these components are to be selected in an overall amount not to exceed 100 wt. %.

While the catalyst used in the process of the present invention or a process for preparing such catalyst may be described in terms of "comprising", "containing" or "including" one or more various described components or steps, it can also "consist essentially of" or "consist of" said one or more various described components or steps.

Within the present specification, "substantially no" means that no detectable amount of the component in question is present in the catalyst or composition.

In the process of present invention, an alkanediol and a dialkyl carbonate are prepared from an alkylene carbonate and an alkanol in the presence of a catalyst which is aluminum phosphate. In the present specification, aluminum phosphate may also be referred to as "AlPO". The anhydrous form of aluminum phosphate or a hydrate of aluminum phosphate may be used in the present invention. Suitable examples of hydrates of aluminum phosphate are $AlPO_4.2H_2O$ and $AlPO_4.1.5H_2O$. Preferably, the anhydrous form of aluminum phosphate is used as the catalyst in the present invention.

The aluminum phosphate catalyst is a heterogeneous catalyst. Further, preferably the aluminum phosphate catalyst in the present invention is amorphous. Preferably, more than 90%, more preferably more than 95%, most preferably more than 99% of the catalyst is amorphous. Preferably, less than 10%, more preferably less than 5%, most preferably less than 1% of the catalyst is crystalline. Most preferably, the catalyst comprises substantially no crystalline structures.

The AlPO catalyst used in the present process may have a molar (or atomic) ratio [Al]/[P] of from 0.1:1 to 20:1, more suitably of from 0.5:1 to 10:1, more suitably of from 1:1 to 5:1, most suitably of from 1.5:1 to 3:1. Preferably, said molar ratio [Al]/[P] is at most 20:1, more preferably at most 15:1, more preferably at most 10:1, more preferably at most 7:1, more preferably at most 5:1, more preferably at most 4:1, more preferably at most 3:1, most preferably at most 2.5:1. Preferably, said molar ratio [Al]/[P] is at least 0.1:1, more preferably at least 0.3:1, more preferably at least 0.5:1, more preferably at least 0.8:1, more preferably at least 1:1, more preferably at least 1.3:1, most preferably at least 1.5:1.

The aluminum phosphate catalyst in the present invention may have a surface area (BET) which varies within a broad range, for example of from 20 to 400 $m^2/g$, suitably of from 50 to 300 $m^2/g$, most suitably of from 100 to 250 $m^2/g$. Further, the AlPO catalyst used in the present process may be provided in the form of a catalyst composition having any shape and any dimensions. For example, the catalyst may be shaped into a tablet form, which may have any shape, for example a cylindrical shape. Furthermore, the catalyst may be shaped in the form of an extrudate. A shaped catalyst composition comprising the AlPO catalyst may additionally comprise a residual amount (for example up to 2 wt. %) of any shaping aid (for example graphite) used when shaping.

In the present invention, naturally occurring aluminum phosphate or synthesized aluminum phosphate may be used as the catalyst. Preferably, synthesized aluminum phosphate is used. Any known method for synthesizing aluminum phosphate may be applied, in order to make the catalyst to be used in the present process. For example, said aluminum phosphate may be synthesized in accordance with any one of the methods as disclosed in U.S. Pat. No. 5,292,701, EP0598464, WO1998018720, WO200174485, WO2007002744 and WO2009136233, the disclosures of which are incorporated herein by reference.

The catalyst used in the present invention may be a catalyst obtained by a process for preparing an aluminum phosphate catalyst, which comprises:

(a) mixing an aluminum containing salt with phosphoric acid in a molar ratio [Al]/[P] of from 0.1:1 to 20:1;

(b) mixing a base with the mixture resulting from step (a), resulting in the formation of an aluminum phosphate precipitate;

(c) optionally heating the precipitate containing mixture; and (d) recovering the precipitate.

In the above-mentioned step (a), the aluminum containing salt may be any salt, for example aluminum nitrate. A hydrate of said salt may be used, for example Al (NO$_3$)$_3$.9H$_2$O or Al(NO$_3$)$_3$.6H$_2$O. Preferably, an aqueous solution containing said salt is used. Further, preferably, an aqueous solution containing phosphoric acid is used. Said aluminum salt containing aqueous solution and said phosphoric acid containing aqueous solution may be mixed in said step (a). The molar ratio [Al]/[P] in the mixture resulting from said step (a) is of from 0.1:1 to 20:1. The preferences for this ratio as described above in relation to the final AlPO catalyst also apply to this mixture obtained in said step (a). Further, the molar concentration (in mole/liter) of aluminum (Al$^{3+}$) in the mixture resulting from said step (a) may be of from 0.1 to 1.8 molar, and is preferably of from 0.2 to 1.3 molar, more preferably of from 0.2 to 0.9, more preferably of from 0.3 to 0.7, most preferably of from 0.3 to 0.6. Still further, the molar concentration (in mole/liter) of phosphate (PO$_4^{3-}$) in the mixture resulting from said step (a) may be of from 0.05 to 1.2 molar, and is preferably of from 0.1 to 0.8 molar, more preferably of from 0.1 to 0.6, more preferably of from 0.15 to 0.45, most preferably of from 0.15 to 0.35.

In the above-mentioned step (b), mixing a base with the mixture resulting from step (a) initiates precipitation of aluminum phosphate. The base may be added to the mixture resulting from step (a), or the mixture resulting from step (a) may be added to the base, or both. Preferably, the base is added to the mixture resulting from step (a). Preferably, an aqueous solution containing the base is used. Said base may be any base, for example ammonia. Preferably, the amount of base used in step (b) is sufficient to achieve a pH in the range of from 4 to 7, suitably of from 4.5 to 6.5, more suitably of from 5 to 6.

In the above-mentioned optional step (c), the aluminum phosphate precipitate containing mixture is heated, suitably at a temperature of from 20 to 100° C., more suitably 20 to 95° C., most suitably 70 to 95° C. Said heating may be performed for a period of from 1 to 10 hours, suitably 1 to 5 hours, more suitably 2 to 4 hours. This treatment in step (c) may be referred to as "ageing".

In the above-mentioned step (d), the aluminum phosphate precipitate is recovered. This may for example be done by filtering the precipitate containing mixture. The aluminum phosphate (precipitate) may then be washed with water and subsequently dried, for example at a temperature of from 50 to 250° C., suitably 70 to 150° C. The aluminum phosphate precipitate recovered in step (d) may have a (volume-based) median pore diameter, before any later calcining step and/or shaping step, which is in the range of 1 to 100 nanometers (nm), more suitably of from 5 to 80 nm, more suitably of from 10 to 60 nm, more suitably of from 15 to 45 nm. Said pore diameter may be determined by a mercury (Hg) intrusion method.

Further, the recovered aluminum phosphate may be subjected to a heat treatment at a temperature of from 200 to 1000° C., suitably 400 to 800° C., more suitably 500 to 700° C. Said heat treatment may be carried out in an inert gas atmosphere or in air, preferably in air. Said heating may be performed for a period of from 1 to 10 hours, suitably 1 to 5 hours, more suitably 2 to 4 hours. This heat treatment may be referred to as "calcining".

Still further, the recovered aluminum phosphate may be shaped into any form, for example tablets, preferably after first milling and/or sieving. The mesh size used when sieving may be any, suitably of from 600 to 1800 μm, more suitably of from 1000 to 1400 μm. The sieved material having a size below said mesh size may be used in such shaping. In case the catalyst is calcined, as described above, such calcination may be performed before and/or after such shaping, preferably after.

The amount of AlPO catalyst used in the present process may vary within wide ranges and should be sufficient to catalyze the desired reaction.

The process of the present invention includes the reaction of an alkylene carbonate with an alkanol. Said alkylene carbonate may be a C$_2$-C$_6$ alkylene carbonate, more suitably a C$_2$-C$_4$ alkylene carbonate, most suitably a C$_2$-C$_3$ alkylene carbonate. Preferably, said alkylene carbonate is ethylene carbonate or propylene carbonate, most preferably ethylene carbonate. The nature of the alkylene carbonate determines the nature of the alkanediol product: for example, reaction of ethylene carbonate with an alkanol results in monoethylene glycol, which is 1,2-ethanediol (the alkanediol). Further, said alkanol may be a C$_1$-C$_4$ alkanol, more suitably a C$_1$-C$_3$ alkanol, most suitably a C$_1$-C$_2$ alkanol. Preferably, said alkanol contains 1 or 2 hydroxy groups, most preferably 1 hydroxy group. Further, preferably, said alkanol is methanol, ethanol or isopropanol, more preferably methanol or ethanol, most preferably ethanol. The nature of the alkanol determines the nature of the dialkyl carbonate product: for example, reaction of an alkylene carbonate with ethanol results in diethyl carbonate (the dialkyl carbonate).

The conditions in the present process include a temperature of from 10 to 200° C., and a pressure of from 0.5 to 50 bara (5×10$^4$ to 5×10$^6$ N/m$^2$). Preferably, especially in co-current operation, said pressure ranges from 1 to 20 bar, more preferably 1.5 to 20 bar, most preferably 2 to 15 bar, and said temperature ranges from 30 to 200° C., more preferably 40 to 170° C., most preferably 50 to 150° C.

Further, preferably an excess of the alkanol over the alkylene carbonate is used in the present process. The molar ratio of alkanol to alkylene carbonate in the present process is suitably of from 1.01:1 to 25:1, preferably of from 2:1 to 20:1, more preferably of from 3:1 to 15:1, most preferably from 3:1 to 13:1.

Still further, the weight hourly space velocity (WHSV) in the present process may suitably range of from 0.1 to 100 kg/kg$_{cat}$.hr ("kg$_{cat}$" refers to the catalyst amount), more suitably 0.5 to 50 kg/kg$_{cat}$.hr, more suitably 1 to 20 kg/kg$_{cat}$.hr, more suitably 1 to 10 kg/kg$_{cat}$.hr.

The present process may be carried out in a reactive distillation column, as described in U.S. Pat. No. 5,359,118. This would entail that the reaction is carried out countercurrently. The distillation column may contain trays with bubble caps, sieve trays, or Raschig rings. The skilled person will realise that several types of packings of catalyst and several tray configurations will be possible. Suitable columns have been described in, e.g., Ullmann's Encyclopedia of Industrial Chemistry, 5$^{th}$ ed. Vol. B4, pp 321 ff, 1992.

The alkylene carbonate will generally have a higher boiling point than the alkanol. In the case of ethylene and propylene carbonate the atmospheric boiling points are above 240° C. Therefore, in general, the alkylene carbonate will be fed at the upper part of a reactive distillation column and alkanol will be fed at the lower part of such column. The alkylene carbonate will flow downwardly, and the alkanol will flow upwardly.

Preferably, the present process is conducted in a co-current manner. A suitable way to operate is to carry out the reaction in a trickle-flow manner wherein the reactants part in vapour phase and part in liquid phase drip down over the catalyst. A more preferred way to operate the process of the present invention is in a reactor with only liquids. A suitable reaction zone of this type is a pipe-type reaction zone wherein the reaction is conducted in a plug flow manner. For example, the present process may be carried out in one plug flow reactor or in a series of two or more plug flow reactors. This will enable the reaction to approach equilibrium.

A further possibility is to conduct the process of the present invention in a continuously stirred tank reactor (CSTR). In the latter case the effluent from the CSTR is preferably subjected to a post-reaction in a plug flow reactor so that the reaction can approach equilibrium.

The process of the present invention is preferably carried out continuously. Further, in the present process, unconverted alkylene carbonate and alkanol are preferably recycled.

The alkanediol and dialkyl carbonate products in the effluent produced by the present process may be recovered in any known way. For example, they may be recovered by applying the process as disclosed in WO2011039113, the disclosure of which is incorporated herein by reference.

The invention is further illustrated by the following Examples.

EXAMPLES

A) Manufacture of Aluminum Phosphate (AlPO) Catalyst

An aluminum phosphate (AlPO) catalyst was prepared as follows.

2 Moles of $Al(NO_3)_3 \cdot 9H_2O$ was dissolved in 3 liters of deionized water. Under vigorous stirring, 1 liter of a solution which contained 1 mole of phosphoric acid was fed, with a feed rate of 2.5 liters/hour, to the aluminum nitrate solution. The precipitation of aluminum phosphate was initiated by feeding aqueous ammonia (10 wt. %) under vigorous stirring, with a feed rate of 2.5 liters/hour, to the above-mentioned solution. The ammonia dosage was stopped when a pH of 5.5 is reached. Then the whole batch was heated up to 90° C. When said temperature of 90° C. was reached, said stirring was continued for a period of time of 2-3 hours. After said ageing step, the precipitate was filtered and the resulting filter cake was washed with water and then dried at 130° C.

The surface area (BET) of said dried precipitate material was 220 $m^2/g$. Further, said aluminum phosphate precipitate material had a (volume-based) median pore diameter of 28 nanometers (nm), as determined by Hg intrusion. Still further, said aluminum phosphate precipitate was amorphous and comprised substantially no crystalline structures.

Then said precipitate material was milled and sieved using a sieve having a mesh size of 1200 μm. The sieved material (having a size below 1200 μm) was mixed with graphite, which is a tabletting aid, and shaped into 3 mm×3 mm tablets of cylindrical shape. The prepared tablets were calcined at 600° C. in air for 3 hours.

In the final AlPO catalyst, the molar/atomic ratio [Al]/[P] was 1.9:1. The surface area (BET) of the final catalyst was 159 $m^2/g$.

B) Use of Aluminum Phosphate (AlPO) Catalyst in the Reaction of Ethylene Carbonate with Ethanol The aluminum phosphate (AlPO) catalyst thus prepared was used in the reaction of ethylene carbonate (eC) with ethanol (EtOH), thereby producing monoethylene glycol (MEG) and diethyl carbonate (DEC). One or more undesired by-products may be formed. The presence of a relatively large amount of by-products is indicative for a relatively lower selectivity towards the desired MEG and DEC products. An intermediate in said reaction is 2-hydroxyethyl ethyl carbonate (HEC) from which one or more of said undesired by-products may be formed. One by-product is 2-ethoxy ethanol. Other by-products are diethylene glycol (DEG), triethylene glycol (TEG) and heavy dimer carbonates (formed from dimerization of 2 HEC molecules).

In Example 1, 165 g of the catalyst were loaded into a tubular stainless steel reactor (internal diameter=32.5 mm, length=2346 mm). The remainder of the reactor was filled with inert glass beads (3 mm). The reactor was externally heated to 130° C. by heating coils and the temperature in the reactor was measured by thermowells inside the catalyst bed.

The reactor was fed in up-flow mode from a feed vessel, which vessel contained ethanol and ethylene carbonate (molar ratio ethanol:EC=5:1), at a feed rate of 750 g/h. The liquid hourly space velocity (LHSV) was 3.2 $1/l_{cat}$.h; the weight hourly space velocity (WHSV) was 4.6 $kg/kg_{cat}$.h; and the reactor pressure was 10-12 bara. Conversion and selectivity over the reactor was measured by GC analysis of the reactor inlet and outlet.

The reactor outlet stream was subjected to distillation, as follows:

a) The top stream comprised light components (EtOH and DEC); and the bottom stream comprised heavy components.

b) Said top stream comprising light components was further distilled, resulting in a top stream comprising EtOH which was recycled to the reactor feed vessel, and a bottom stream comprising DEC which was further distilled to produce 99.9+ wt. % pure DEC.

c) Said bottom stream comprising heavy components was further distilled, resulting in a top stream comprising MEG in an azeotropic mixture with 15-17 wt. % of EC, and a bottom stream comprising EC and heavier by-products which latter bottom stream was partly recycled to the reactor feed vessel.

The unit comprising the reactor and distillation columns was operated in continuous mode with closed recycles. Fresh ethanol and EC were dosed to the reactor feed vessel, which also contained unreacted/recycled ethanol and EC, to maintain an ethanol:EC molar ratio of 5:1.

In steady operation, the EC conversion in Example 1 was 46%. Said conversion and the selectivities to the desired products DEC and MEG, to HEC, and to the 2-ethoxy ethanol by-product and to other by-products, including DEG, TEG and dimer carbonates, are shown in Table 1 below.

No leaching of the AlPO catalyst to the reactor outlet stream was observed in Example 1. The aluminum (Al) concentration in the reactor effluent and distillation column bottom streams remained below the Al-detection limit of 50 parts per billion by weight (ppbw), as determined by ICP analysis ("ICP" stands for "Inductively Coupled Plasma").

In Examples 2-6, some parameters regarding the reaction of EC with EtOH in the reactor were varied, as shown in Table 1 below.

TABLE 1

| | Example | | | | | |
|---|---|---|---|---|---|---|
| | 1 | 2 | 3 | 4 | 5 | 6 |
| Catalyst type | AlPO | AlPO | AlPO | AlPO | AlPO | Zn·Cr$_2$O$_3$ |
| Amount catalyst (g) | 165 | 165 | 302 | 302 | 302 | 1800 |
| Temperature (° C.) | 130 | 130 | 130 | 130 | 145 | 130 |
| Feed rate (g/h) | 750 | 600 | 1000 | 550 | 1000 | 750 |
| LHSV (l/l$_{cat}$ · h) | 3.2 | 2.6 | 2.3 | 1.3 | 2.3 | 1.0 |
| WHSV (kg/kg$_{cat}$ · h) | 4.6 | 3.6 | 3.3 | 1.8 | 3.3 | 0.4 |
| EC conversion (%) | 46 | 48 | 52 | 60 | 60 | 51 |
| Sel. to DEC (mol %) | 57 | 58 | 60 | 66 | 69 | 55 |
| Sel. to MEG (mol %) | 56 | 57 | 58 | 64 | 67 | 52 |
| Sel. to HEC (mol %) | 36 | 33 | 32 | 25 | 23 | 36 |
| Sel. to 2-ethoxy ethanol (mol %) | 0.09 | 0.07 | 0.11 | 0.13 | 0.20 | 0.40 |
| Sel. to other by-products (mol %) | 6 | 6 | 5 | 6 | 6 | 10 |

Sel. = selectivity

The Zn.Cr$_2$O$_3$ catalyst used in Example 6 (reference) is commercially available at BASF (Zn-0312-T1/8-HT). Said catalyst contained 59 wt. % of Zn, 15 wt. % of Cr and had a surface area of 13 m$^2$/g. In above-mentioned WO2004024658, the use of a Zn.Cr$_2$O$_3$ catalyst in the reaction of propylene carbonate with methanol is described.

Upon comparing the results of Examples 1-5 (invention) with those of Example 6 (reference), it appears that the aluminum phosphate (AlPO) catalyst used in the present process has the following advantages over the reference (Zn.Cr$_2$O$_3$) catalyst.

First of all, as shown in Table 1 above, in Example 6 (reference) a similar EC conversion was obtained as in Example 3 (invention). However, in Example 6 (reference) the selectivities to DEC and MEG were significantly lower: 55 versus 60% (DEC) and 52 versus 58% (MEG). The selectivities to DEC and MEG in Example 6 (reference) were lower when compared with all of Examples 1-5 (invention).

Further, in Example 6 (reference) the selectivity to the 2-ethoxy ethanol by-product was significantly higher (0.40 mol %) than when using the AlPO catalyst in Examples 1-5 (invention) which was only in the order of 0.07-0.20 mol %.

Further, in Example 6 (reference) the selectivity to other by-products, including DEG, TEG and dimer carbonates, was also significantly higher (10 mol %) than when using the AlPO catalyst in Examples 1-5 (invention) which was only in the order of 5-6 mol %.

Still further, the AlPO catalyst is more active than the reference (Zn.Cr$_2$O$_3$) catalyst. In order to obtain a similar EC conversion, significantly less catalyst is required in Examples 1-5 (invention). This can be seen for example by comparing the LHSV and WHSV in Example 3 with the lower LHSV and WHSV in Example 6 (reference), at a similar EC conversion of 51-52%.

Overall, when comparing all of Examples 1-5 (invention) with Example 6 (reference), the productivity to the desired DEC and MEG products is advantageously higher.

Finally, with the Zn.Cr$_2$O$_3$ catalyst used in Example 6 (reference), leaching of zinc (Zn) was observed, in the order of 20-70 ppbw of Zn in the reactor outlet stream. On the other hand, as already mentioned above, with the AlPO catalyst used in Examples 1-5 (invention), no leaching of aluminum (Al) to the reactor outlet stream was observed at all.

That which is claimed is:

1. A process for the preparation of an alkanediol and a dialkyl carbonate comprising reacting an alkylene carbonate and an alkanol in the presence of a catalyst, wherein the catalyst is aluminum phosphate.

2. The process according to claim 1, wherein the aluminum phosphate catalyst is amorphous.

3. The process according to claim 2, wherein more than 90% of the catalyst is amorphous.

4. The process according to claim 1, wherein the aluminum phosphate catalyst has a molar (or atomic) ratio [Al]/[P] of from 0.1:1 to 20:1.

5. The process according to claim 1, wherein the aluminum phosphate is synthesized aluminum phosphate.

6. The process according to claim 5, wherein the aluminum phosphate catalyst is a catalyst obtained by a process for preparing an aluminum phosphate catalyst, which comprises:
  (a) mixing an aluminum containing salt with phosphoric acid in a molar ratio [Al]/[P] of from 0.1:1 to 20:1;
  (b) mixing a base with the mixture resulting from step (a), resulting in the formation of an aluminum phosphate precipitate;
  (c) optionally heating the precipitate containing mixture; and
  (d) recovering the precipitate.

7. The process according to claim 1, wherein the alkylene carbonate is a C$_2$-C$_6$ alkylene carbonate.

8. The process according to claim 7, wherein the alkylene carbonate is ethylene carbonate or propylene carbonate.

9. The process according to claim 1, wherein the alkanol is a C$_1$-C$_4$ alkanol.

10. The process according to claim 9, wherein the alkanol is methanol, ethanol or isopropanol.

* * * * *